United States Patent [19]

Dobson

[11] Patent Number: 5,709,839
[45] Date of Patent: Jan. 20, 1998

[54] MULTI-SENSOR SYSTEMS

[75] Inventor: John Vincent Dobson, Hartlepool, Great Britain

[73] Assignee: The Secretary of State for Defence in Her Britannic Majesty's Government of the United Kingdom of Great Britain and Northern Ireland, Hants, United Kingdom

[21] Appl. No.: 604,985

[22] PCT Filed: Sep. 13, 1994

[86] PCT No.: PCT/GB94/01994

§ 371 Date: Apr. 23, 1996

§ 102(e) Date: Apr. 23, 1996

[87] PCT Pub. No.: WO95/08112

PCT Pub. Date: Mar. 23, 1995

[30] Foreign Application Priority Data

Sep. 14, 1993 [GB] United Kingdom ............... 9318940

[51] Int. Cl.[6] .................... G01N 27/416; G01N 35/08
[52] U.S. Cl. ............... 422/81; 422/68.1; 436/43; 436/52; 436/174; 436/179; 436/180
[58] Field of Search ............ 422/68.1, 81, 103, 422/63, 67; 436/43, 52, 174, 179, 180

[56] References Cited

U.S. PATENT DOCUMENTS

| 3,690,833 | 9/1972 | Ferrari | 422/81 |
|---|---|---|---|
| 4,680,271 | 7/1987 | Williams | 436/55 |
| 4,705,669 | 11/1987 | Tsuji et al. | 422/93 |
| 4,818,348 | 4/1989 | Stetter | 104/1 T |
| 4,865,811 | 9/1989 | Newton et al. | 422/81 |
| 5,019,515 | 5/1991 | Gisin et al. | 436/52 |
| 5,055,260 | 10/1991 | Roberge et al. | 422/62 |
| 5,108,928 | 4/1992 | Menard et al. | 436/43 |
| 5,212,095 | 5/1993 | Miki et al. | 436/52 |

*Primary Examiner*—Long V. Le
*Attorney, Agent, or Firm*—Nixon & Vanderhye P.C.

[57] ABSTRACT

A multi-sensor flow-through system which mitigates or at least overcomes any cross field effects between different sampling conduits comprising a plurality of flow-through sample cells (2), wherein each sample cell (2) is provided in an independent and isolated sample channel (16a, 16b...), whereby fluid flowing within each channel (16a, 16b, ...) is isolated from fluid flowing in neighboring channels (16a, 16b, ...). In one embodiment of the multi-sensor system, each sensor cell (2) operates as an autonomous and independent unit isolated from all other units. Ideally, each of the sample channels (16a, 16b, ...) are also independent and isolated from other sample channels (16a, 16b...). The multi-sensor system can additionally have the exit end of the channels (16a, 16b, ...) feed into a well in such a way that free space is provided between the ends of the channels and the uppermost surface of fluid in the well. A further improvement is the use of a single inlet conduit (15) which passes through at least one reagent chamber (4, 5, 6), whereby at least reagent is added to the sample before the reagent supplemented sample passes into the plurality of sampling channels (16a, 16b, ...).

4 Claims, 1 Drawing Sheet

MULTI-SENSOR SYSTEMS

BACKGROUND OF THE INVENTION

1. Field of the Invention

The invention relates to a flow through multi-sensor system including a plurality of sensing cells whereby a number of readings can be taken particularly, but not exclusively, simultaneously.

2. Discussion of the Prior Art

When monitoring solutions for the presence of additives or contaminants it is preferable to use a flow-through sample system and further, to use a sample system which is adapted to take a number of readings so as to identify the presence of a plurality of contaminants. Ideally, the sample system is adapted to take a number of readings simultaneously.

One method for sampling a solution involves the electrochemical accumulation of ionic species from an aqueous solution at a conducting substrate, followed by removal of that species from the substrate by the application or reversal of current. This technique is called Anodic Stripping Voltammetry (ASV).

In ASV, almost universally, a discrete sample is employed. However, some anodic stripping devices that have been patented allow for a flowing sample, although the overall process, whilst being periodic in its operation, is not continuous. That is to say a single sample is taken and a complicated program then ensues. Meanwhile the flow is stopped in the sample gathering part of the apparatus. As a consequence of the protracted nature of the process, periods of an hour for it's duration are not uncommon. Thus, the analytical result is of value only to very slowly changing conditions, or where the speed of update is unimportant.

Whilst anodic stripping is mainly carried out on solid substrates, improvement with mercury drop polarographic equipment in recent years, in the form of the hanging (HMD)/static mercury drop technique has allowed the use of this technique in ASV.

Unprecedented sensitivities are now commonplace with this type of polarographic equipment when applied to ASV. Although somewhat limited to a laboratory bench environment because of it's fragile nature, and whilst still mainly restricted to discrete samples, the application of electronic/ electrochemical pulsing techniques, prior to and during the stripping cycle, allows sensitivities to reach at least $10^{-1}$ parts per billion for a wide range of inorganic ion and organic species. One such technique is Differential Pulse Anodic Stripping Voltammetry (DPASV).

DPASV has become a competitor for Atomic Absorption Spectroscopy (AAS) in terms of its comparable sensitivity and more importantly, no sample pre-treatment is usually necessary. In addition, when an adsorptive mode is applied, sensitivity may be increased to $10^{-2}$ parts per billion.

It will be apparent from the above that, before a chemical species can be identified using ASV, it is necessary to determine the key markers for each particular species to be determined. For example, the deposition, accumulation, reduction and oxidation potentials for each species; the flow rate of the sample, the sweep rate, the pulse rate and its magnitude; the nature of the signal response, whether it is curved or linear relative to the concentration range, the temperature effects or cross sensitivities.

The above characteristics must be identified for all those metals to be identified, and also for all of the organic species to be identified which are electrochemically detectable such as, $NO_2$, —NO, —CO, —N=N—, —C=C— etc, and therefore molecules such as, for example, nitro phenyls, azo and diazo compounds, quinones, aldehydes, ketones, and unsaturated compounds with double bonds such as styrene etc.

Thus, to quote some specific examples. For Lindane, DDT and BHC and Dieldrin the analysis relies upon the reduction of carbon-halogen bond. PCNB,2,4,dinitro-6-cyclohexylphenol, methyl parathion, all contain reducible nitro groups. Compounds such as sodium diethyl dithiocarbamate and methylenebisthiocynanate are detectable due to the presence of the sulphur-hydrogen and thiocyanide groups, etc.

Moreover, each of these certain groupings make their own particular contribution to the overall energy requirement for the reduction processes, or practically, the potential where there is a significant reduction rate of the molecule.

Thus, and especially for complex or substituted compounds, more than one peak may be identified in a voltage scan for such molecules. This has the advantage of finger printing a large number of molecules. There are published texts which are wholly devoted to measured and some calculated halfwave potentials (reduction potentials) of organic species which may be consulted.

A second often important factor is the role of pH. For example, the reduction of the carbon-halogen bond is independent of the pH value. This factor may be exploited. Therefore significant changes in the reduction process by way of its facility and reduction routes etc may be the result of attempted reduction in acid or alkaline media. Here again, the peak potential shifts may be used to good effect for electrochemical analysis.

Despite obtaining all the aforementioned knowledge, it is well known that multi-sensor systems often fail to operate or produce spurious results. The precise reason for this is unknown. It has been suggested that it may be related to the configuration and operation of conventional systems. For example, a typical multi-sensor system comprises a plurality of sensing cells through which a given solution flows. The arrangement is such that the solution is delivered to the sensor cells via a single conduit which divides into a plurality of sampling conduits. After a measurement is taken, the sampling conduits converge to form a single exit conduit. This arrangement could encourage cross-field effects between different sensing cells since, at the site of sensor cell convergence, the effects of each sensing potential will still be present. Thus, there is a possibility that cross-field effects can take place.

European Patent Application EP 0,529,155 A1 discloses a continuous flow anodic or cathodic stripping voltammeter which is capable of taking into account the effects of interfering species during analysis of a fluid sample for a particular species. The device comprises two sample cells, through which the sample solution flows. One sample cell analyses the fluid sample by measuring the dissolution current over a potential range characteristic of the particular ionic or molecular species of interest with that ionic species present in the sample solution, the other cell measuring the dissolution current over a potential range characteristic of the particular ionic or molecular species of interest with the ionic species having been removed from the fluid sample. The two results are subtracted from each other. The fluid samples from the two sample cells then mix together down stream of the sample cells. The arrangement disclosed in this application can suffer from cross-field effects as described previously. Similarly, if several such devices are used in conjunction with each other to form a multi-sensor system, the system would suffer from the cross-field effects unless measure such as those disclosed within this application were taken.

The document International Laboratory, vol. 13, no. 7, September 1983, J Wang "On line sensors for trace metals" discloses an on-line stripping analysis system for stripping analysis. However, the document does not disclose any means or method to overcome cross-field effects.

SUMMARY OF THE INVENTION

The object of the invention is to provide a multi-sensor system which overcomes, or at least mitigates, this cross-field activity.

However, it may be that such cross-field activity is not responsible for the spurious readings typically associated with conventional systems. The suggestion for the reason for such spurious readings is not intended to adversely affect the scope of the invention. Rather, the invention relies on the provision of apparatus which overcomes spurious readings characteristic of the prior art regardless of the underlying scientific reasoning.

According to the present invention there is provided a multi-sensor flow through system for the detection of certain materials within a fluid sample comprising a plurality of flow through sensor cells wherein each sensor cell is provided in an independent and isolated sample channel, the exit end of each sample channel feeding into a well, the multi-flow through sensor system being arranged such that, when the sample fluid flows through the multi-sensor flow through system:

the fluid flowing through each sample channel is isolated from the fluid flowing in the other sample channels; and there is free space provided between the exit ends of the sample channels and the upper most surface of any fluid within the well, the fluid having to pass through the free space before mixing with the fluid in the well to ensure that there are no cross-field effects between the different sample solutions in each sample channel.

In the above arrangement, the invention ensures that the sample solution in each sample channel is mixed only at a site remote from the sensor system, after passing through free space. This ensures that no cross-field effects between different sample solutions can take place.

In one embodiment of the invention, each sensor cell operates as an autonomous and independent unit isolated from all other units and further, each sample channel is also independent and isolated from other sample channels such that cross-channel effect is avoided.

Preferably the apparatus includes a single inlet conduit which passes through at least one reagent chamber whereby at least one reagent is added to the fluid sample before the reagent supplemented fluid sample passes into said plurality of sampling channels.

BRIEF DESCRIPTION OF THE FIGURE

An embodiment of the invention will now be described, by way of example only, with reference to the accompanying FIGURE which is a schematic representation of a multi-sensor apparatus in accordance with the invention.

DETAILED DISCUSSION OF PREFERRED EMBODIMENTS

Figure 1:
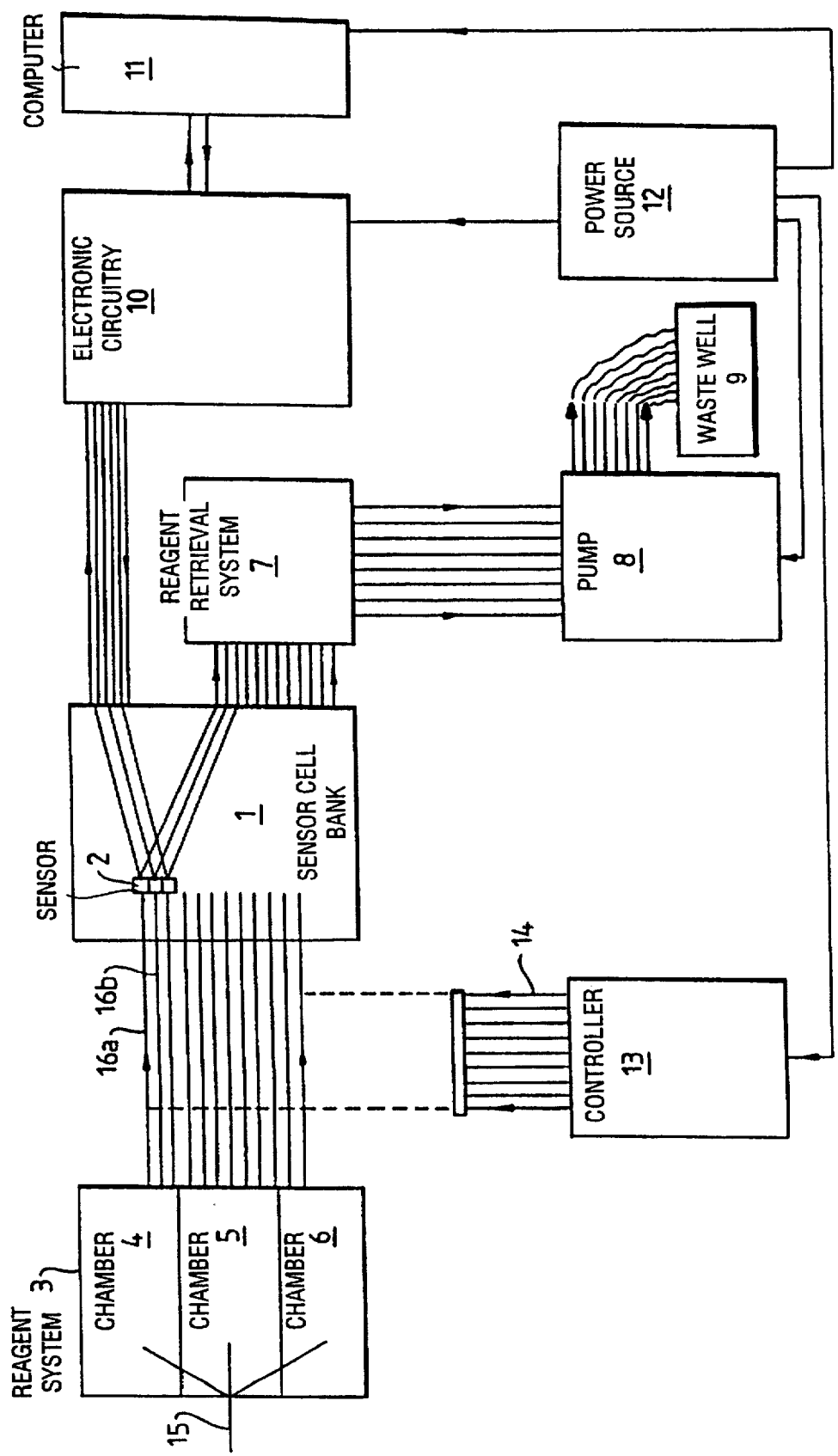

The FIGURE shows a multi-sensor system including a sensor cell bank 1 including a plurality of sensors 2 wherein each sensor 2 is adapted to take a pre-selected ASV reading so as to identify the presence of a pre-selected chemical species within a sample solution. Sensors 2 may be arranged in any preferred array.

Upstream of said sensor system 1 there is provided a reagent system 3 including chambers 4, 5 and 6. Chamber 4 is adapted to allow at least one pre-selected reagent to a sample solution, for example a buffering reagent so as to control the pH of the sample solution. Chamber 6 is adapted to add at least one pre-selected ligand to the sample solution with a view to facilitating the identification of a ligand specific chemical species.

Downstream of said sensor system 1 there is provided a waste reagent retrieval system 7. System 7 is optional.

Downstream of sensor 1 and/or system 7 there is provided a pump means 8 adapted to pump the sample solution to waste 9.

Electronic circuitry 10 is provided downstream of sensor system 1 and connected thereto such that sampling information from sensors 2 can be accessed and interrogated by a computer (PC) 11.

A power source 12 is provided for operation the electronics 10 and computer 11 and also pump 8.

A control means 13 comprising valve means may be provided for controlling the passage of reagents and particularly mercury ions through the system. Ideally, at least one valve is provided within each sample channel. The valve means are connected by a valve control lines 14 to the control means 13. Each conduit is ideally provided with a valve means so that mercury ions can be directed to all cells simultaneously for plating purposes.

The multi-sensor system is provided with an inlet 15 comprising a single inlet conduit. The sample solution enters reagent system 3 and ideally traces a route that passes through chambers 4, 5 and 6 so that it is exposed to pre-selected resins, reagents, ligands and the like.

After the sample solution has been supplemented or conditioned in the aforementioned manner, the sample solution exits from the reagent system 3 and enters a plurality of independent and isolated conduits 16a, 16b, each provided with a single sensor cell 2. Since each sensor cell 2 will be adapted to measure, via ASV, the concentration of a pre-selected chemical species within the sample solution, each sensor cell 2 will have a characteristic electrochemical signature. This signature will be determined according to the chemical species to be identified. Thus, each sample solution passing through each sensor cell will experience a different electrochemical field. Once a reading has been taken the results of this reading will pass via electronic system 10 to computer 11 where the reading will be interrogated and interpreted. The results of this process will then be displayed on suitable means for an operator to read.

Sample solution passing through sensor cells 2 remains in sample channels 16a, 16b, 16c, 16d ... 16nth and may enter a waste reagent retrieval system.

Waste reagent retrieval system 7 may be any conventional system such as the provision of ion exchange resins or the like. Alternatively, techniques used in ASV may be applied for stripping each channel of a pre-selected chemical species. Thus, for each channel an appropriate electrode would be provided and a potential would be applied to such electrode such that a chemical species was removed. This may be repeated so as to remove a plurality of chemical species.

After passage through waste reagent retrieval system 7, independent and isolated sample channels 16a, 16b, 16c, 16d ... 16nth then pass via pump 8 to a sample waste well 9.

throughout the above, sample channels 16a, 16b, 16c, 16d ... 16nth remain isolated and separate.

As shown in the FIGURE, sample channels 16a, 16b, 16c, 16d ... 16nth feed into a waste well 9, the ends of the sample channels being positioned above the upper most surface of the solution within the well so that fluid leaving the sample channels passes through free space before mixing occurs within the well. Thus, contact between sample solution in adjacent sample channels is avoided until after electrochemical contact between adjacent sample solution is effectively cut.

The provision of an electrochemical multi-sensor system including a plurality of isolated and independent sample channels overcomes the spurious readings associated with the prior art and thus enable multi-sensor readings to be taken using ASV techniques. This has not hitherto been possible. We have therefore unexpectedly provided a way of operating a multi-sensor electrochemical system by simply isolating each sample channel and associated sensor cell.

I claim:

1. A multi-sensor flow through system for detection of certain materials within a fluid sample, said system comprising:

a plurality of flow through sensor cells wherein each sensor cell is provided in an independent and isolated sample channel, a chamber for providing said fluid sample to each of said sample channels a waste well, an exit end of each sample channel feeding into said waste well, wherein said fluid sample flowing through each sample channel is isolated from said fluid sample flowing in another channel; and a free space provided between the exit ends of the sample channels and the waste well, the fluid sample in each channel having to pass through the free space before mixing with a fluid in the waste well thereby ensuring that there are no cross-field effects between sample solutions in different sample channels.

2. A multi-sensor system as claimed in claim 1 wherein each sensor cell operates as an autonomous and independent unit isolated from other sensor cells.

3. A multi-sensor system as claimed in claim 2 wherein each sample channel is also independent and isolated from other sample channels.

4. A multi-sensor system as claimed in claim 1 wherein the system further includes:

at least one reagent chamber; and a single inlet passing said fluid sample into said reagent chamber, whereby at least one reagent is added to the fluid sample before the fluid sample passes into the plurality of sampling channels.

* * * * *